(12) United States Patent
Diamond et al.

(10) Patent No.: US 6,264,615 B1
(45) Date of Patent: Jul. 24, 2001

(54) METHOD FOR DIAGNOSING THE PRESENCE AND EXTENT OF HALITOSIS ACTIVITY

(75) Inventors: Howard Diamond, Ann Arbor; Donald L. Musinski, Saline, both of MI (US)

(73) Assignee: Diamond General Development Corporation, Ann Arbor, MI (US)

( * ) Notice: Subject to any disclaimer, the term of this patent is extended or adjusted under 35 U.S.C. 154(b) by 0 days.

(21) Appl. No.: 09/487,753

(22) Filed: Jan. 19, 2000

Related U.S. Application Data (60) Provisional application No. 60/116,799, filed on Jan. 21, 1999.

(51) Int. Cl.[7] .................................................. A61B 5/08
(52) U.S. Cl. ........................................ 600/530; 600/345
(58) Field of Search .................................. 600/345–350, 600/530

(56) References Cited

U.S. PATENT DOCUMENTS

| | | | |
|---|---|---|---|
| 3,507,269 | * 4/1970 | Berry | 600/530 |
| 4,823,803 | 4/1989 | Nakamura | 128/717 |
| 4,922,921 | * 5/1990 | Donoghue | 600/530 |
| 5,275,161 | 1/1994 | Graves et al. | 128/635 |
| 5,628,312 | 5/1997 | Musinski | 128/734 |
| 5,833,955 | * 11/1998 | Kleinberg et al. | 424/49 |

* cited by examiner

*Primary Examiner*—Robert L. Nasser
(74) *Attorney, Agent, or Firm*—Gifford, Krass, Groh, Sprinkle, Anderson & Citkowski, P.C.

(57) ABSTRACT

A method and apparatus for diagnosing the presence and extent of halitosis activity are disclosed. A method includes assaying for the presence of sulfides on the surface of a subject's tongue in order to determine the concentrations of sulfides in the fluids.

12 Claims, 6 Drawing Sheets

METHOD FOR DIAGNOSING THE PRESENCE AND EXTENT OF HALITOSIS ACTIVITY

RELATED APPLICATION

This application claims priority of U.S. Provisional Application Ser. No. 60/116,799 filed Jan. 21, 1999.

FIELD OF THE INVENTION

The subject invention generally relates to the field of detecting halitosis or bad breath and, more particularly, to an improved method for measuring the concentration of sulfides within the mouth of a subject to determine the presence and extent of halitosis activity.

BACKGROUND OF THE INVENTION

Halitosis, commonly known as bad breath, is a common concern for many people. The most common source of halitosis is thought to be the tongue. Gram negative, anaerobic bacteria are prone to proliferate in the papilla structure at the posterior or rear of the tongue. The papilla form a multitude of niches or irregularities which are favored breeding grounds for the anaerobic bacteria as they simulate non-oxygenated micro environments. The anaerobic bacteria break down specific components such as amino acids found in the saliva generating or producing sulfur containing metabolic by-products. These sulfur containing by-products are volatile and have been implicated as the major cause of odor and/or halitosis. It is interesting to note that these same bacteria which are associated with the causation of halitosis are often the same bacteria considered as the etiological agent for periodontal disease.

The detection and diagnosis of halitosis has traditionally involved self-monitoring which is typically accomplished by breathing into one's own hand and then sniffing the trapped contents or a person suspecting that they have halitosis can utilize another person to sample their breath and render a subjective diagnosis.

Devices or monitors for the detection of halitosis are known in the art. U.S. Pat. No. 4,823,803, to Nakamura, issued Apr. 25, 1989, discloses a device for testing human exhalation for halitosis. Other prior art devices are known for analyzing a subject's breath for volatile sulfur emissions.

U.S. Pat. No. 5,275,161, hereby incorporated by reference, assigned to the same assignee as the subject invention, discloses a method and apparatus for electrochemically detecting and quantifying sulfide levels in gingival sulci to determine the presence and extent of gingivitis and periodontal disease in a subject. The method disclosed therein employs a probe which is inserted into the sulcus and which includes a miniature sulfide measuring electrode and a reference electrode. U.S. Pat. No. 5,628,312 also assigned to the same assignee as the subject invention, discloses a probe for diagnosing periodontal disease by the concentration of sulfides present which includes a sulfide responsive measuring electrode and a reference electrode joined by a salt bridge to assure electrical continuity between the sulfide responsive electrode and the reference electrode.

Accordingly, it would be advantageous and desirable to have a method for diagnosing the presence and extent of halitosis activity on the surface of a subject's tongue by measuring the concentration of sulfides thereon.

SUMMARY OF THE INVENTION

There is disclosed a method for diagnosing the presence and extent of halitosis activity in a subject by measuring the concentration of sulfides present on the surface of the subject's tongue. The method includes the step of assaying fluid disposed on the surface of the tongue for the concentration of sulfides therein.

There is also disclosed a method for diagnosing the presence and extent of halitosis activity in the mouth of a subject by measuring the concentration of sulfides present on the surface of the subject's tongue including the steps of providing a sulfide responsive probe. A preferred probe includes a housing having a tip configured to probe the surface of the tongue, a measuring electrode and a reference electrode operative to establish an electrical potential therebetween when the tip is contacted with a sulfide containing fluid wherein the electrical potential generated is proportional to the concentration of sulfides in the fluid.

There is also disclosed a method for diagnosing the presence and extent of halitosis activity on the surface of a subject's tongue by measuring the concentration of sulfides thereon including the steps of providing a dual electrode probe having a sulfide-responsive measuring electrode and a reference electrode, providing a voltage indicator for generating a data readout reflective of the strength of the electrical potential between the sulfide-responsive measuring electrode and the reference electrode, and electrically connecting the sulfide-responsive measurement electrode and the reference electrode to the voltage indicator. The probe is then positioned in contact with the surface of the subject's tongue such that both electrodes are in contact with the surface of the tongue and the fluid disposed thereon wherein the fluid bridges the electrodes to cause a potential between the sulfide-responsive measurement electrode and the reference electrode, whereby the magnitude of the potential corresponds to the concentration of the sulfides in the fluid. The method further includes the steps of reading the data readout provided by the voltage indicator which is indicative of the concentration of sulfides on the surface of the tongue and comparing the data readout with a predetermined standard to determine the extent of halitosis.

BRIEF DESCRIPTION OF THE DRAWINGS

The following detailed description is best understood with reference to the following drawings in which.

DETAILED DESCRIPTION OF THE INVENTION

Figure 1:
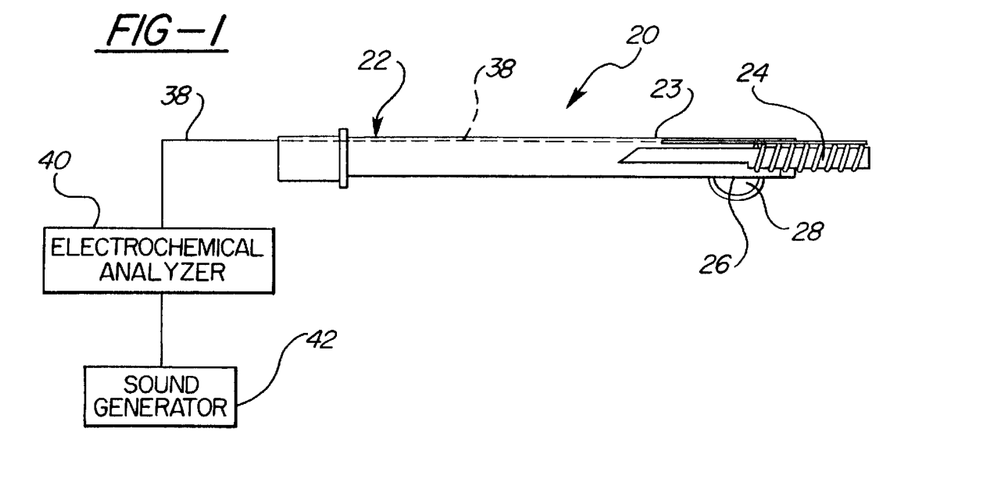
FIG. 1 is a depiction of a probe structured in accordance with the present invention.
Figure 2:
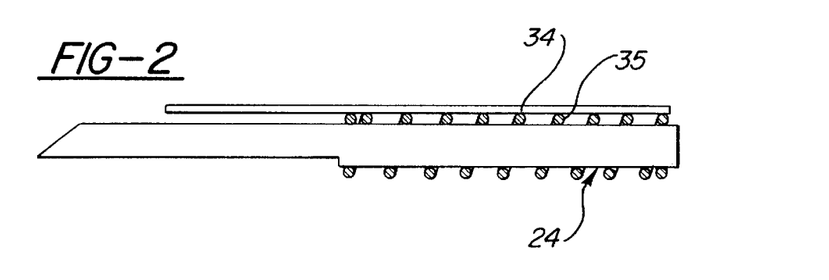
FIG. 2 is an enlarged, cross-sectional view of a portion of the probe of FIG. 1.
Figure 3:
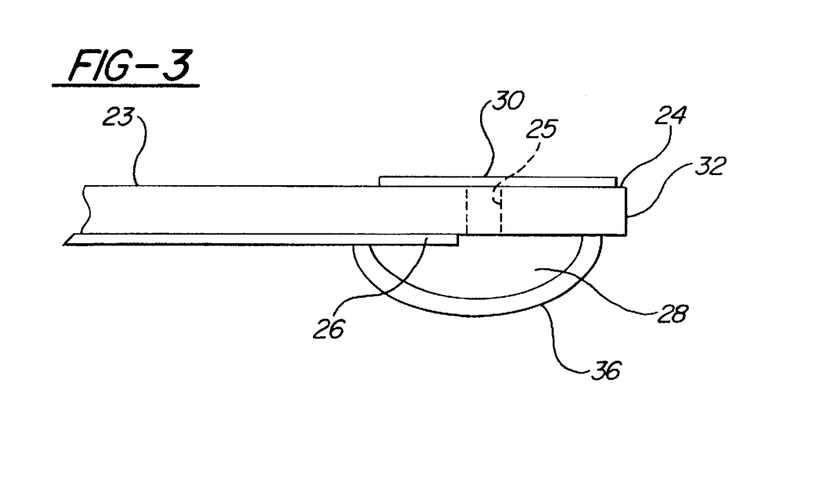
FIG. 3 is an enlarged, cross-sectional view of a portion of the probe of FIG. 1.

The present invention is directed to a halitosis probe for measuring the sulfide concentration of fluids disposed in the mouth or oral cavity, specifically on the surface of the tongue. Suitable probes include those disclosed in either U.S. Pat. No. 5,275,161 and/or U.S. Pat. No. 5,628,312 both incorporated herein by reference. Referring to FIGS. 1 and 2, a typical probe structure 20 in accordance with the principles of the present invention is shown. The probe 20 includes a housing 22 which can be disposable having a dimension and shape configured to contact or probe various regions of the surface of the tongue and also which contains a sulfide-responsive sensing electrode 24. The probe 20 further includes a reference electrode 26 supported by the housing 22 or by an optional disposable second housing portion 23. Referring to FIGS. 1 and 3, the reference electrode 26 is immersed within a salt pellet 28 to control the chemical environment. The reference electrode 26 is kept in electrical contact with the sulfide-responsive sensing electrode 24 through a salt bridge 30. An aperture 25 is disposed within the probe assembly 20 to provide direct electrical contact to the salt bridge when hydrated.

As shown in U.S. Pat. Nos. 5,275,161 and/or 5,268,312, the sulfide-responsive measuring electrode 24 and the reference electrode 26 are connected to respective, electrically conductive leads 38. The leads 38 are in electrical communication with an electro-chemical analyzer 40 which may operationally include a sound generator 42 in communication therewith.

In operation, the probe 20 is disposed so that a tip portion 32 thereof is in contact with the fluid layer disposed on the subject's tongue so that the sulfide-responsive electrode 24 contacts the fluid. The reference electrode 26 is also in electrical communication with the fluid, via the salt bridge 30. An electrical potential is developed between the sulfide-responsive electrode 24 and the reference electrode 26 and this electrical potential is proportional to the sulfide concentration in the fluid. The electro-163 chemical analyzer is operative to sense the potential between the electrodes 24,26 and to provide a display which is directly indicative of, or correlatable with, sulfide concentration. Since, in some instances, it is difficult for a practitioner to observe a visual display while properly positioning the probe 20 on the tongue, the sound generator 42 may be utilized in combination with the electro-chemical analyzer 40. The sound generator 42 produces an audible signal which is indicative of the potential generated between the electrodes 24,26.

Referring to FIG. 2, the sulfide-responsive measuring electrode 24 is most preferably fabricated from a material which undergoes an electro-chemical reactivation with the sulfide ion. One particularly preferred material comprises silver sulfide and, accordingly, the electrode 24 may be simply comprised of a fine sulfided silver wire 34 with an insulator 35 disposed therebetween. In other instances, the electrode 24 may comprise a wire, such as a stainless steel wire, coated with silver. Other metals reactive with sulfide may be similarly employed, for example, antimony.

The reference electrode 26 is disposed in an electrochemical relationship with the sulfide-responsive electrode 24 and must be employed in order to provide a potential indicative of a sulfide ion concentration.

In a preferred embodiment, the reference electrode 26 is disposed in the probe 20. One particularly preferred reference electrode 26 comprises a silver-silver chloride electrode, typically provided by disposing a chloride coating on a silver wire 34. In some instances, the chloride coating will be disposed to cover a substantial length of the wire, and in other instances, the wire will be insulated along substantially all of its length and will have a body of silver chloride disposed so as to cover a free end of the wire. All such configurations may be employed in the practice of the present invention.

The reference electrode 26 is disposed within the pellet 28 of a salt, such as potassium chloride. The pellet 28 of potassium chloride can be partially covered by the material of the housing 22, and preferably has a major portion of its free surface covered by a moisture impervious material, such as a layer of epoxy resin.

In accordance with another feature of the present invention, as shown in FIG. 3, there is provided a hydration layer 36 on the probe 20, in the region of the reference electrode 26, sulfide-responsive electrode 24 and salt bridge 30. The hydration layer 36 comprises a smooth, open structured, over-coated layer which assures the maintenance of hydrated conditions between the electrodes 24,26 and salt bridge 30 and allows for wider tolerances in the fabrication of the salt bridge 30. A number of different materials may be utilized for the hydration layer 36. One preferred material involves cellulose acetate. Other embodiments of the hydration layer 36 may similarly be prepared from a variety of polymers such as cellulose acetate-butyrate, vinyls and the like.

In use, once the probe 20 is hydrated, the probe 20 is ready for insertion into the mouth of the subject and for contact with the surface of the subject's tongue. The probe 20 is inserted so that it comes into contact with the fluid layer overlying the tongue. The electrolytes within the fluid layer will cause an electrical potential to develop between the electrodes 24,26, the magnitude of which corresponds to the concentration of sulfide in the fluid.

After measurement of the tongue, a portion of or all of the probe 20 may be discarded as the probe 20 is preferably made of or constructed of disposable materials.

While one particular configuration of the probe 20 has been illustrated, it will be appreciated that in accordance with the principles disclosed herein, other configurations may be implemented.

The present invention can be utilized to record localized measurements of sulfide concentrations on the surface of the tongue for day-to-day variations, variations within a single day, for the effect of normal activities (eating, drinking), and for the effective treatment modalities, such as mouthwashes, as illustrated in the examples set forth below. Additionally, as sulfide concentrations are not necessarily uniform over the entire surface of the tongue, the probe of the present invention can be utilized to detect points and/or regions of the surface of the tongue which may be "hot spots" where sulfide production is located or unusually high.

EXAMPLES

The following examples are presented in order to demonstrate the utility of the present invention.

EXAMPLE 1

Figure 4:
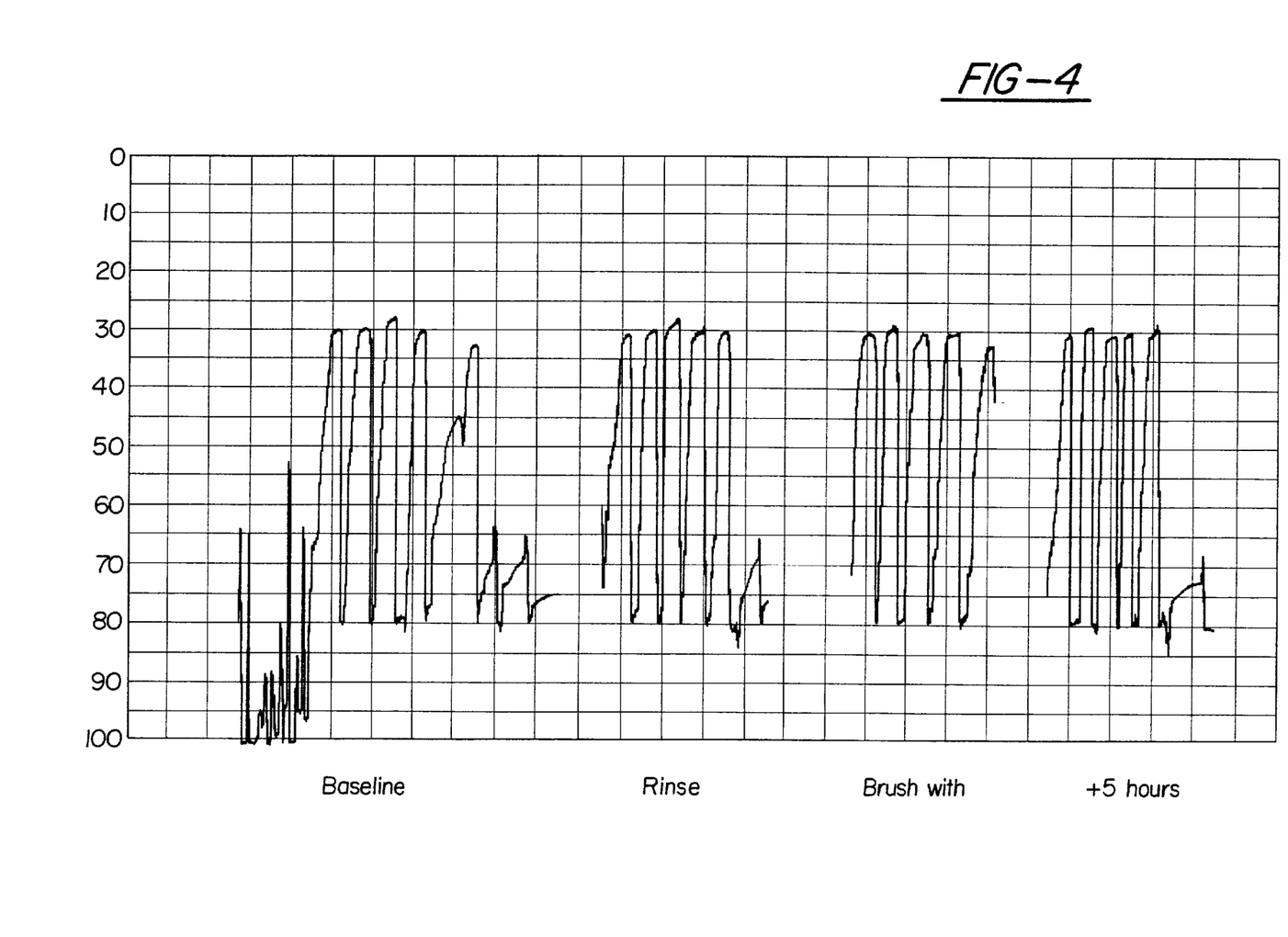
FIG. 4 is a graph depicting sulfide levels on the surface of a subject's tongue treated with artificial saliva.

Example 1 demonstrates the ineffectiveness of an artificial saliva product for altering the sulfide concentrations on the surface of a tongue of a subject. Referring to FIG. 4, the sulfide concentrations taken over time are displayed as a function of signal strength in millivolts.

Baseline data was obtained from the tongue of an experimental subject. Five measurements from the surface of the tongue including rear center, rear left, rear right, left side, and right side were obtained. One measurement from underneath the tongue was also obtained. The measurements were then repeated immediately following the subject's rinsing for thirty seconds with a commercially available artificial saliva product. The subject then brushed their tongue with a toothbrush dipped into the artificial saliva product and the six measurements were immediately taken again. Five hours after the initial rinse with the artificial saliva product, the six measurements were again repeated.

The data obtained in this example demonstrate the uniformity and repeatability of sulfide measurements obtained utilizing the probe of the present invention. The artificial saliva product, as expected, had no effect on the sulfide concentrations measured on the surface of the subject's tongue.

EXAMPLE 2

In this example, the effectiveness of the bactericide chlorhexidine for the reduction of sulfide levels on the surface of a subject's tongue was analyzed. It was predicted that chlorhexidine would be effective in the reduction of sulfide levels on the surface of the tongue as it is known that chlorhexidine is retained by oral tissue.

As in Example 1, measurements of the sulfide levels on the surface of the tongue and from the underside of the tongue were obtained utilizing the probe of the subject invention.

Figure 5:
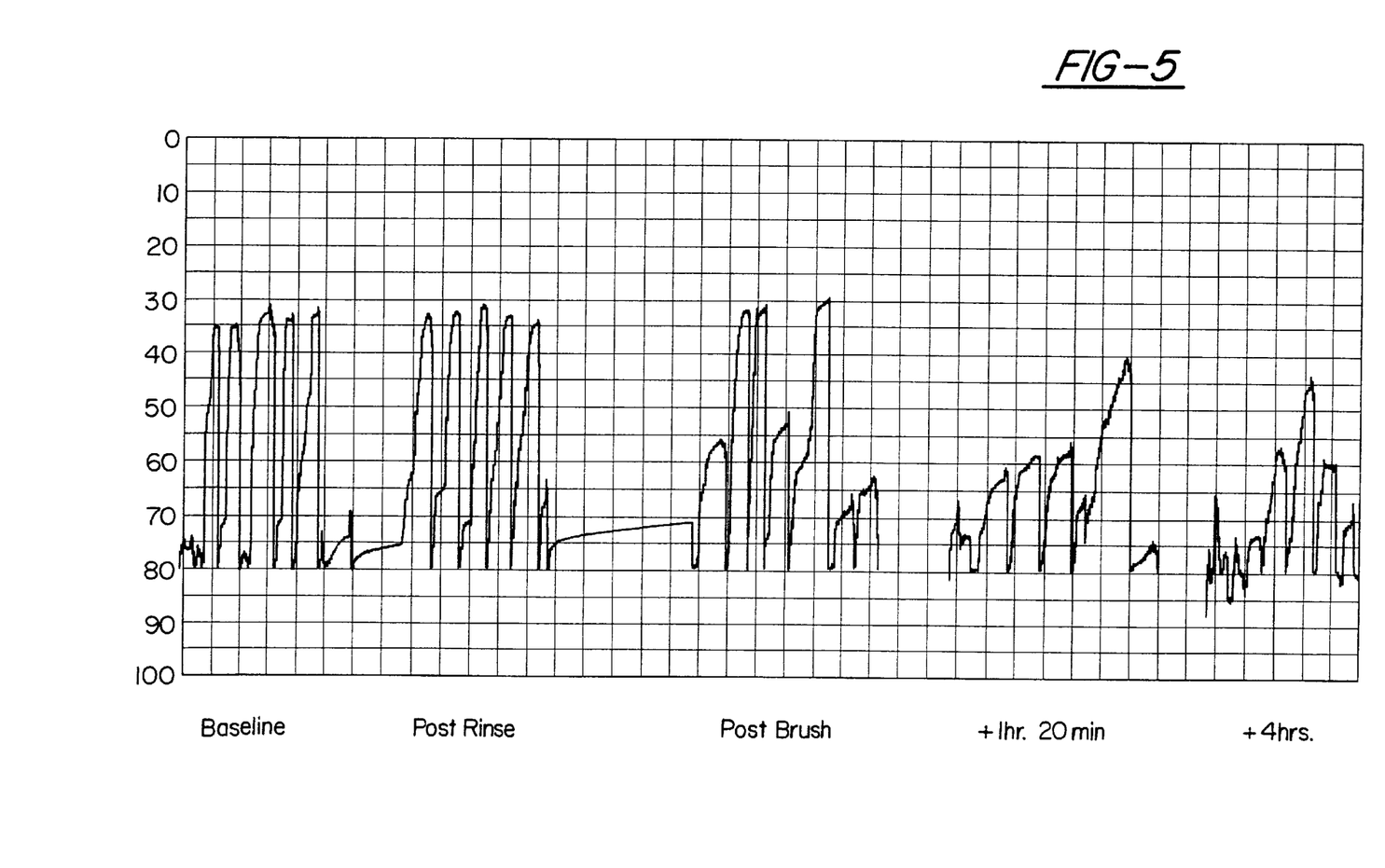
FIG. 5 is a graph depicting sulfide levels on the surface of a subject's tongue treated with 0.12% chlorhexidine.

Referring to FIG. 5, the results of the chlorhexidine experiment are shown. Baseline data was obtained from the surface of the tongue and from underneath the tongue as described in Example 1. The measurements were then repeated immediately following a thirty second rinse of the subject's tongue in 0.12% chlorhexidine. The subject then brushed their tongue with a toothbrush which had been dipped into the 0.12% chlorhexidine solution. As shown in FIG. 5, two of the five measurements from the surface of the tongue are reduced significantly. After a one hour and twenty minute time delay following the initial chlorhexidine rinse, the measurements were repeated and four of the five measurements from the surface of the tongue were reduced considerably. The fifth measurement had also been significantly reduced. After a four hour delay following the initial chlorhexidine rinse, the six measurements were repeated. Four of the five measurements from the surface of the tongue were found to be lower than those recorded at the one hour and twenty minute time point. The fifth measurement was higher than that recorded at the one hour and twenty minute interval but was considerably lower than the initial measurement.

The data obtained in this example was found to be consistent with the documented modality or action of chlorhexidine. That is, there is no immediate reduction in sulfide concentration; however, after the passage of a period of time, the retained chlorhexidine residue destroys contacted bacteria thus shutting down the production of sulfides by the bacteria. As the time progresses, more and more bacteria are destroyed at some sites while at other sites the bacteria is able to proliferate once again. This example demonstrates the utility of the probe of the present invention in obtaining sulfide concentrations which are correlatable to the action of a known bactericide.

EXAMPLE 3

Figure 6:
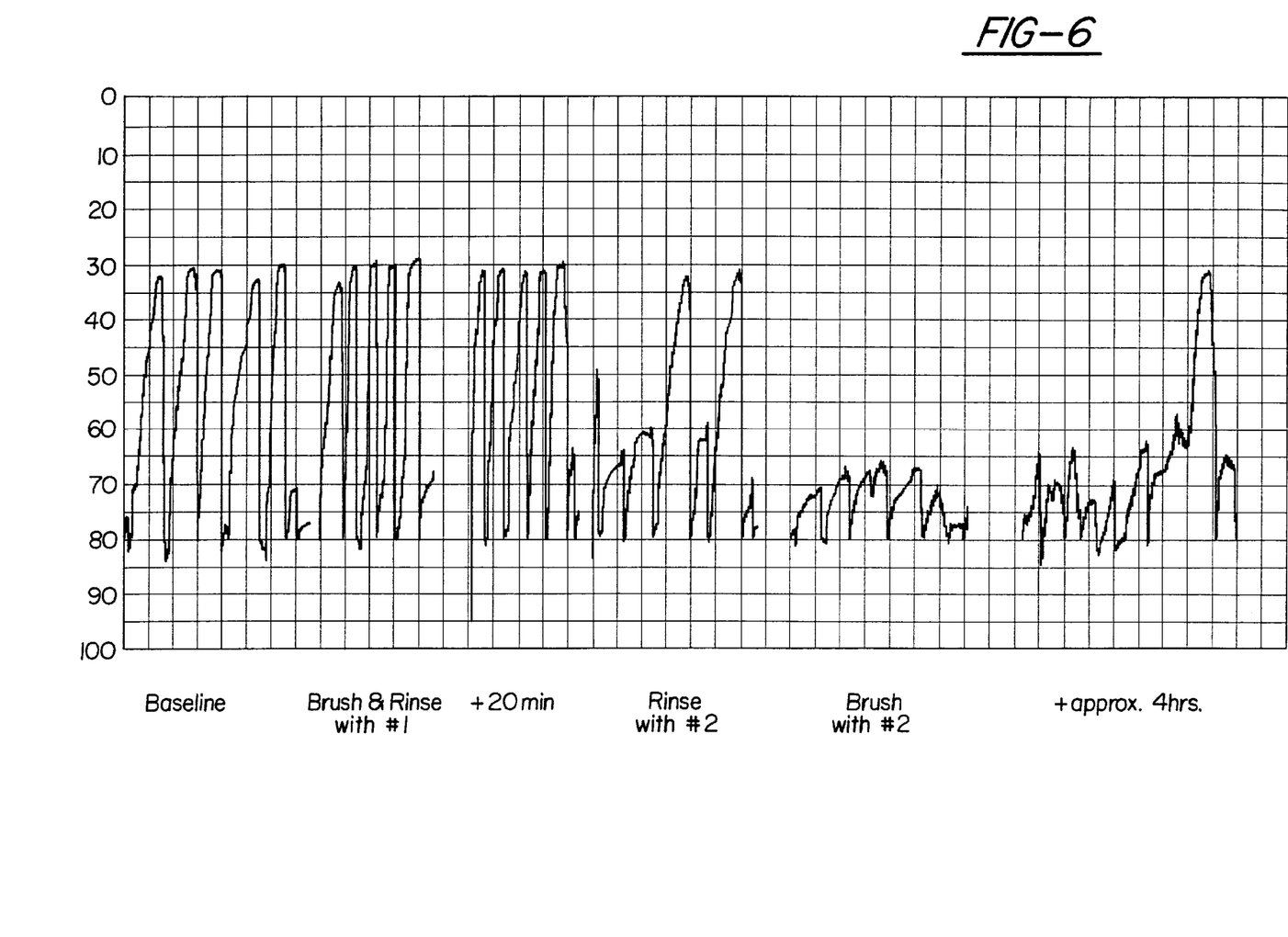
FIG. 6 is a graph depicting sulfide levels on the surface of a subject's tongue treated "back to back" with a first commercially available product and a second commercially available product.

In Example 3, a first and a second commonly available commercial oral hygiene product were administered in a "back-to-back" fashion. Referring to FIG. 6, the data obtained in this example are illustrated. As in Example 1, measurements of the concentration of sulfides on the surface of the tongue and underneath the tongue were obtained utilizing a probe in accordance with the present invention. A baseline was established by obtaining five measurements of the surface of the subject's tongue and one measurement from underneath the subject's tongue. Immediately thereafter, the subject brushed and rinsed with the first product and then the six measurements were immediately obtained. Then, following a twenty minute time period, the six measurements were repeated. Then, the subject rinsed with the second product for thirty seconds and the six measurements were taken. Three of the five measurements of the sulfide concentration were found to be significantly lower with the other two being slightly reduced. The subject then brushed with the second product and the measurements were again repeated. All measurements on the surface of the tongue were significantly reduced. After a period of four hours from the initial brush and rinse with the first product, four of the five measurements from the surface of the tongue remained significantly lowered while one of the measurements had increased to the level seen immediately after the rinse with the second product.

Based on this "back-to-back" comparison, the first product was found to be ineffective for reducing the sulfide concentrations on the surface of the subject's tongue, the second product was found to have an immediate effect which could be increased by mechanically manipulating the surface of the tongue by brushing. After 4 hours, there was evidence that bacterial generation of sulfides were recurring.

EXAMPLE 4

Figure 7:
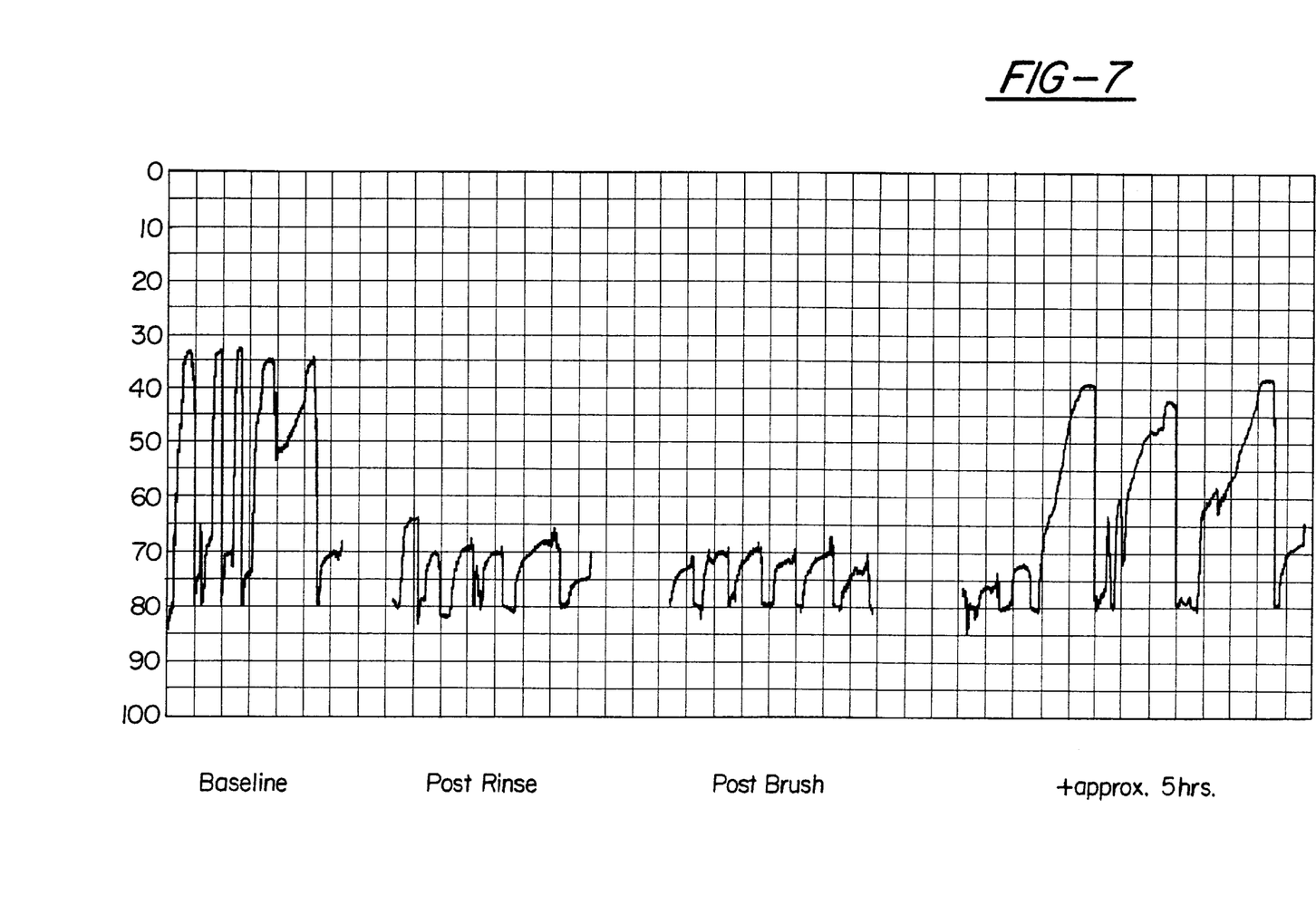
FIG. 7 is a graph depicting sulfide levels on the surface of a subject's tongue treated with a third commercially available product.

In this example, another product comprising a third commonly available commercial oral hygiene product was tested as shown in FIG. 7. Measurements were obtained as in Example 1. A baseline was established by taking five measurements of the sulfide concentration from the surface of the subject's tongue. One measurement was taken from underneath the tongue. The subject then rinsed with the product, and the six measurements were repeated thirty seconds thereafter. All five surface measurements indicated a significant lowering of the sulfide concentrations. The subject then brushed with a toothbrush which had been dipped in the product and the measurements were immediately repeated thereafter. Very little additional reduction of sulfide concentration was found. Five hours after the initial rinse, the measurements were repeated. Two of the five surface measurements were found to remain very low. The remaining three of the five signals had begun to increase approaching the initial baseline values.

The product tested appears to produce an immediate significant reduction of sulfide production. Some of the sulfide production areas were kept sulfide free for more than five hours. Other areas were found to again produce sulfide within this time interval.

EXAMPLE 5

Figure 8:
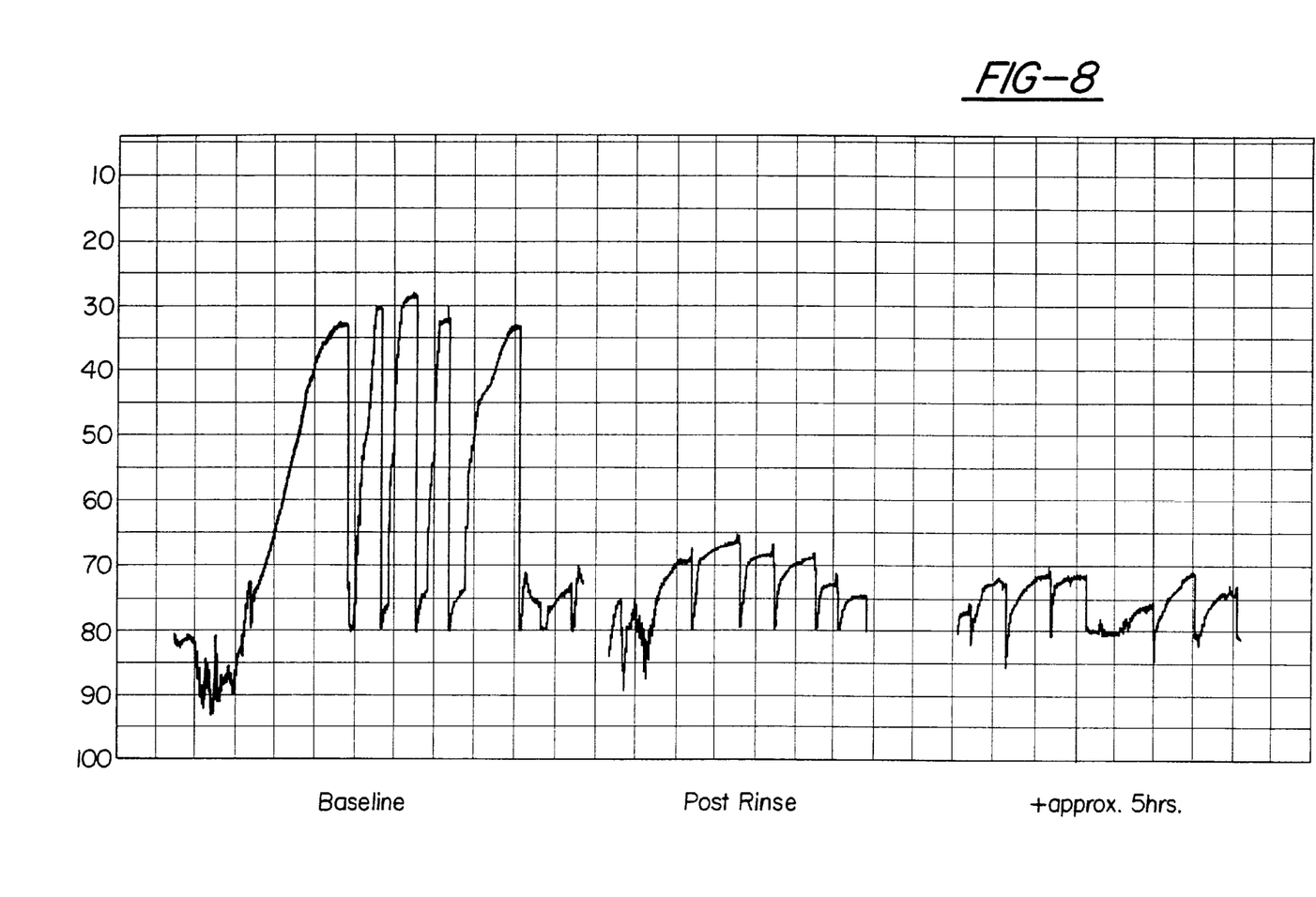
FIG. 8 is a graph depicting sulfide levels on the surface of a subject's tongue treated with a fourth commercially available product.

In this example, a product comprising a fourth commonly available commercial oral hygiene product was tested for its ability to lower sulfide concentrations on the surface of a subject's tongue as shown in FIG. 8. Measurements were taken as described for the previous examples utilizing a probe in accordance with the present invention. A baseline measurement was obtained and thereafter the subject rinsed twice with the product. Thirty seconds after the second rinse, the six measurements were immediately taken. It was found that all five surface sulfide concentrations had been considerably reduced. Five hours after the rinse, the measurements were repeated and all five of the surface sulfide concentration measurements indicated that all five sulfide concentration measurements were considerably reduced.

The product tested in this example demonstrated an immediate and significant reduction of sulfide production. Even five hours after the initial treatment, sulfide production remained very low and sulfide production had not been reestablished.

The foregoing examples demonstrate the ability of the probe of the present invention to be utilized for obtaining measurements of the sulfide levels on the surface of the tongue. These measurements can be used for the diagnosis of halitosis and to assess the effectiveness of treatments for halitosis.

In view of the teachings presented herein, other modifications and variations of the present inventions will be readily apparent to those of skill in the art. The foregoing drawings, discussion, and description are illustrative of some embodiments of the present invention, but are not meant to be limitations on the practice thereof. It is the following claims, including all equivalents, which define the scope of the invention.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

What is claimed:

1. A method for diagnosing the presence and extent of halitosis activity on the surface of a subject's tongue by measuring the concentration of sulfides thereon, said method comprising the steps of:

providing a dual electrode probe having a sulfide-responsive measuring electrode and a reference electrode;

providing a voltage indicator for generating a data readout reflective of the strength of the electrical potential between the sulfide-responsive measuring electrode and the reference electrode;

electrically connecting the sulfide-responsive measurement electrode and the reference electrode to the voltage indicator;

positioning the probe in contact with the surface of the subject's tongue such that both electrodes are in electrical contact with the surface of the tongue and the fluid disposed thereon wherein the fluid bridges the electrodes to cause a potential between sulfide-responsive measurement electrode and the reference electrode, the magnitude of the potential corresponds to the concentration of sulfides in the fluid;

reading the data readout provided by the voltage indicator and indicative of the concentration of sulfides on the surface of the tongue; and comparing the data readout with a predetermined standard to determine the extent of the halitosis.

2. A method for diagnosing the presence and extent of halitosis activity in the mouth of a subject by measuring the concentration of sulfides present on the surface of the subject's tongue, said method comprising the steps of:

providing a sulfide-responsive probe comprising a housing having a tip configured to probe the surface of the tongue, a measuring electrode and a reference electrode operative to establish an electrical potential therebetween when the tip is contacted with a sulfide containing fluid, the electrical potential being proportional to the concentration of sulfides in the fluid.

3. A probe for diagnosing the presence and extent of halitosis in a subject's mouth by measuring the concentration of sulfides on the surface of the subject's tongue, said probe comprising:

a housing having a first end defining a tip configured to probe the surface of the tongue;

a sulfide-responsive, measuring electrode supported by said housing with a surface portion thereof disposed in said tip so as to establish fluid communication with the fluid when said tip is disposed on the tongue;

a reference electrode supported by said housing at a location which will not contact the fluid when the tip is disposed in the mouth, said reference electrode having a surface portion thereof disposed in a body of a salt;

a salt bridge material which is disposed so as to establish a conductive path between said body of salt and said measuring electrode when the tip is disposed in contact with the fluid on the surface of the tongue;

a first electrical lead in electrical communication with the measuring electrode;

a second electrical lead in electrical communication with the reference electrode;

said probe being operative, when immersed in the fluid, to generate an electrical potential between said measuring electrode and said reference electrode which is proportional to the concentration of sulfide in the fluid; and an electrochemical analyzer for relating said electrical potential to the extent of halitosis.

4. A probe as in claim 3 further including a hydration layer disposed in contact with said salt bridge material.

5. A probe as in claim 4, wherein said hydration layer comprises a porous organic polymer having a salt disposed within said pores.

6. A probe as in claim 5, wherein said organic polymer comprises cellulose acetate.

7. A probe as in claim 3, wherein said body of salt has a major portion of the surface thereof which is covered by a moisture impervious coating and a minor portion thereof which is free of said coating.

8. A probe as in claim 7, wherein said body of salt is a body of potassium chloride.

9. A probe as in claim 3, wherein said salt bridge material comprises an organic matrix having particles of a salt disposed therein.

10. A probe as in claim 9, wherein said organic matrix comprises a polymer.

11. A probe as in claim 10, wherein said polymer comprises an epoxy polymer.

12. A probe as in claim 9, wherein said salt comprises potassium chloride.

* * * * *